United States Patent [19]

Suovaniemi et al.

[11] 4,215,092

[45] Jul. 29, 1980

[54] APPARATUS FOR LIQUID PORTIONING AND LIQUID TRANSFERRING

[75] Inventors: Osmo Suovaniemi, Armas Lindgrenint.15, 00570 Helsinki, Finland; Mikko Leskinen, Vantaa, Finland

[73] Assignee: Osmo A. Suovaniemi, Helsinki, Finland

[21] Appl. No.: 923,534

[22] Filed: Jul. 11, 1978

Related U.S. Application Data

[63] Continuation-in-part of Ser. No. 764,170, Jan. 31, 1977, abandoned.

[30] Foreign Application Priority Data

| Apr. 8, 1976 [FI] | Finland | 760957 |
| Jan. 4, 1977 [DE] | Fed. Rep. of Germany | 2700096 |
| Apr. 6, 1977 [DD] | German Democratic Rep. | 198281 |
| May 9, 1977 [FI] | Finland | 771459 |
| Mar. 1, 1977 [JP] | Japan | 52-22141 |
| Jan. 28, 1977 [GB] | United Kingdom | 3491/77 |
| Mar. 25, 1977 [SU] | U.S.S.R. | 2463804 |

[51] Int. Cl.² ............................................. B01L 3/02
[52] U.S. Cl. ................................. 422/100; 73/425.6; 138/111; 220/23.4; 222/137; 222/267; 222/276; 422/102

[58] Field of Search .................. 422/99, 100, 102; 220/23.2, 23.4, 23.8; 73/425.4 D, 425.6; 222/137, 265, 267, 275, 276; 138/111, 116, 177, 178

[56] References Cited

U.S. PATENT DOCUMENTS

| Re. 27,637 | 5/1973 | Roach | 422/100 X |
| 2,826,339 | 3/1958 | Maillard | 222/137 |
| 3,175,734 | 3/1965 | Heiss | 422/100 X |
| 3,498,135 | 3/1970 | Seitz et al. | 422/100 X |
| 3,498,342 | 3/1970 | Sanderson | 222/137 X |
| 3,545,935 | 12/1970 | Kearns | 220/23.8 X |
| 3,572,552 | 3/1971 | Guinn | 422/99 X |
| 3,785,773 | 1/1974 | Rohrbaugh | 422/102 |
| 3,855,868 | 12/1974 | Suovaniemi | 73/425.6 |
| 3,907,505 | 9/1975 | Beall et al. | 422/102 |
| 3,955,930 | 5/1976 | Shapiro | 73/425.6 X |
| 4,058,370 | 11/1977 | Suovaniemi | 422/100 |

Primary Examiner—Joseph Scovronek
Attorney, Agent, or Firm—Hopgood, Calimafde, Kalil, Blaustein & Lieberman

[57] ABSTRACT

A multichannel pipette is disclosed having an improved arrangement of replaceable tip containers in which the individual tip containers are connected together by flexible connecting members which are deformable to permit connection of the tip containers to differing configurations of tip cones.

5 Claims, 4 Drawing Figures

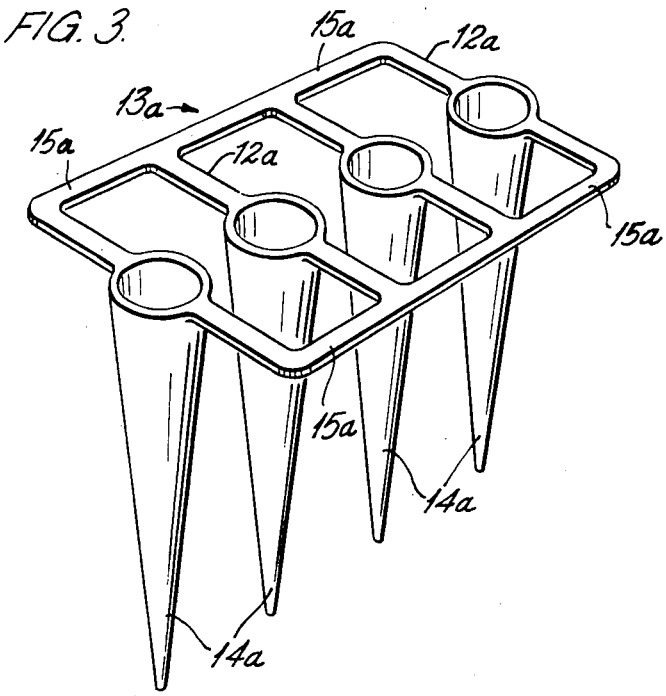
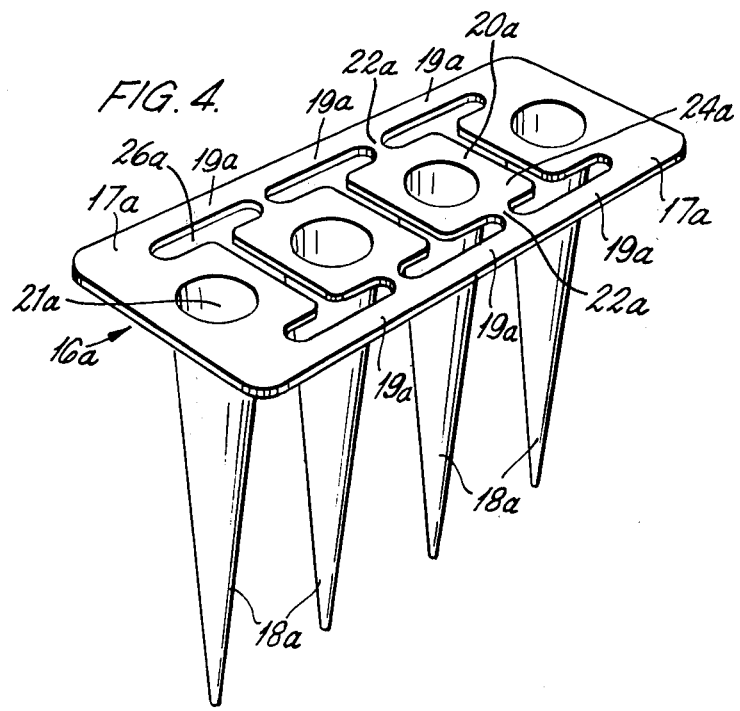

APPARATUS FOR LIQUID PORTIONING AND LIQUID TRANSFERRING

CROSS REFERENCE TO PRIOR APPLICATION

This application is a continuation-in-part of our pending application Ser. No. 764,170 filed Jan. 31, 1977, and now abandoned and hereby incorporates by reference the subject matter of such prior application.

BACKGROUND OF THE INVENTION

This invention relates to apparatus for liquid portioning and/or liquid transferring and specifically to a multichannel pipette and to replaceable tip containers for use with such a multichannel pipette.

In many laboratory determinations, apparatus is needed to transfer small precisely measured amounts of liquid from one tube into another. The system must be simple, rapid, economical, and precise. Transfer of small liquid quantities from one container into another has increased in laboratory applications particularly in connection with many liquid dosages and diluting series utilized in Bacteriology, Immunohaematology, Mycology, Mycoplasma, Parasitology, Rickettsia, Serology, Virology and V.D. Serology.

Liquid transfer may of course be performed in single tube pipettes either of the simple glass tube type or of the adjustable automatic type. When it is desirable to transfer given amounts of liquid from and to a multiplicity of sample containers it is far more economical to utilize apparatus which can transfer several samples simultaneously.

There are prior art systems which permit the transfer of more than one sample. In the system related to the registered trademark "Cooke Microtiter," a plate is used that has 8×12 pits, and the titration from one pit into another is performed by means of one or several microdiluters. These single microdiluters are either held in the hand, or several of them are held in a device which is handheld. Alternatively, they may be mounted in an automatic device placed in a machine. The mixing of the liquid in a pit is performed by rotating the microdiluter back and forth. The microdiluter transfers liquid so that the sample or reagent, due to capillary force, adheres to the calibrated tip portion of the microdiluter. Most commonly, in this system, volumes of 25 and 50 ul are used. The "Cooke Microtiter" involves several drawbacks:

The microdiluters of the system cannot be precisely calibrated, because the filling of the tip portion takes place by capillary force and the tip portion may not empty completely because of dirt, scratches in the glass or other mechanical problem in the tip portion of the device. The residue remaining in the microdiluters can result in contamination of other samples. Because of this, careful cleaning of the microdiluters is necessary after each use. This is expensive and can lead to errors if the cleaning substance is not thoroughly removed.

It is also difficult to vary the volume of this device since there are eight to twelve different volumes of microdiluters and the correct volume must be on hand for each application. This can be both cumbersome and expensive.

Another system on the market is a multichannel pipette sold under the trademark, "Finnpipette." Such a device is disclosed in U.S. Pat. No. 3,855,868. This device utilizes replaceable tip containers. To avoid the problem of contamination and also to avoid the necessity of an expensive and time consuming washing or cleaning after each use.

This device is adjustable over a wide range of volumes by a micrometer adjustment which can provide the necessary precision. It can also be conveniently held and operated in one hand.

Prior art tip container elements were formed in a structure in which several tip containers were connected by a rigid support or connection plate. A tip container element with such a rigid construction can be fitted to the tip cones of only one configuration of a multichannel pipette. Since a multichannel pipette may be constructed with different numbers and arrangements of tip cones depending upon the desired end use, flexibility is needed in the configuration of arrays of tip containers. The present invention provides this needed flexibility.

The present invention improves the above described prior art devices in several important ways. First, it provides an improved arrangement of replaceable tip containers which makes such tip containers easier to use with various multichannel pipette configurations. Second, it provides interchangeable precalibrated handles which can be attached to the body portion of a multichannel pipette. The use of such precalibrated handles avoids the necessity for the accurate setting of the micrometer adjustment of the prior art "Finnpipette" device and permits less skilled laboratory personnel to achieve accurate results quickly and easily.

SUMMARY OF THE INVENTION

A multichannel pipette has a body portion which includes a body housing having first and second opposed ends. A plurality of tip containers for holding liquid communicate with the first end of the body housing. A plurality of cylinders having first and second ends are disposed within the housing with the first end of each of the cylinders communicating with one of the tip containers. A plurality of pistons have first and second ends and each of the second ends of the pistons extend into and are movable within one of the cylinders. A plurality of O rings are included. One of these O rings is disposed within each of the cylinders surrounding and in contact with each of the pistons. Spring bias means are provided to bias the O ring against the second end of the cylinder. A movable member is disposed within the housing and is connected to the first end of each of the piston rods.

A plurality of interchangeable handles are provided. Each handle is preadjusted to dispense a predetermined volume of liquid from the tip containers. Each such handle includes a housing which has first and second opposed ends. A rod is disposed within the housing and has a first end which extends through the first end of the housing. A push button is attached to the first end of the rod. Second spring bias means are provided to bias the rod so that the push button extends a predetermined maximum distance from the housing.

First connecting means are provided to detachably connect the handle housing to the body housing. Second connecting means are provided to detachably connect the second end of the rod to the movable member so that the movable member and the pistons are depressed in response to the depression of the push button to dispense a predetermined quantity of liquid from the tip containers.

An additional feature of the invention is a tip container element which is detachably connectable to the tip cone elements of a multichannel pipette. The tip container element includes a plurality of truncated conical tip containers, which are connected together in a linear configuration. Each of these tip containers includes a base portion which is detachably connectable to one of the tip cone elements of the multichannel pipette. Connecting means are disposed between the base portions of the adjacent tip containers which make up the tip container element. These connecting means include at least one flexible strip-like member having a length greater than the distance between the adjacent cone tip elements of the multichannel pipette.

BRIEF DESCRIPTION OF THE DRAWINGS

FIG. 3 is a perspective view of a second embodiment of the tip container element.

FIG. 4 is a perspective view of a third embodiment of the tip container element.

DETAILED DESCRIPTION

Figure 1:
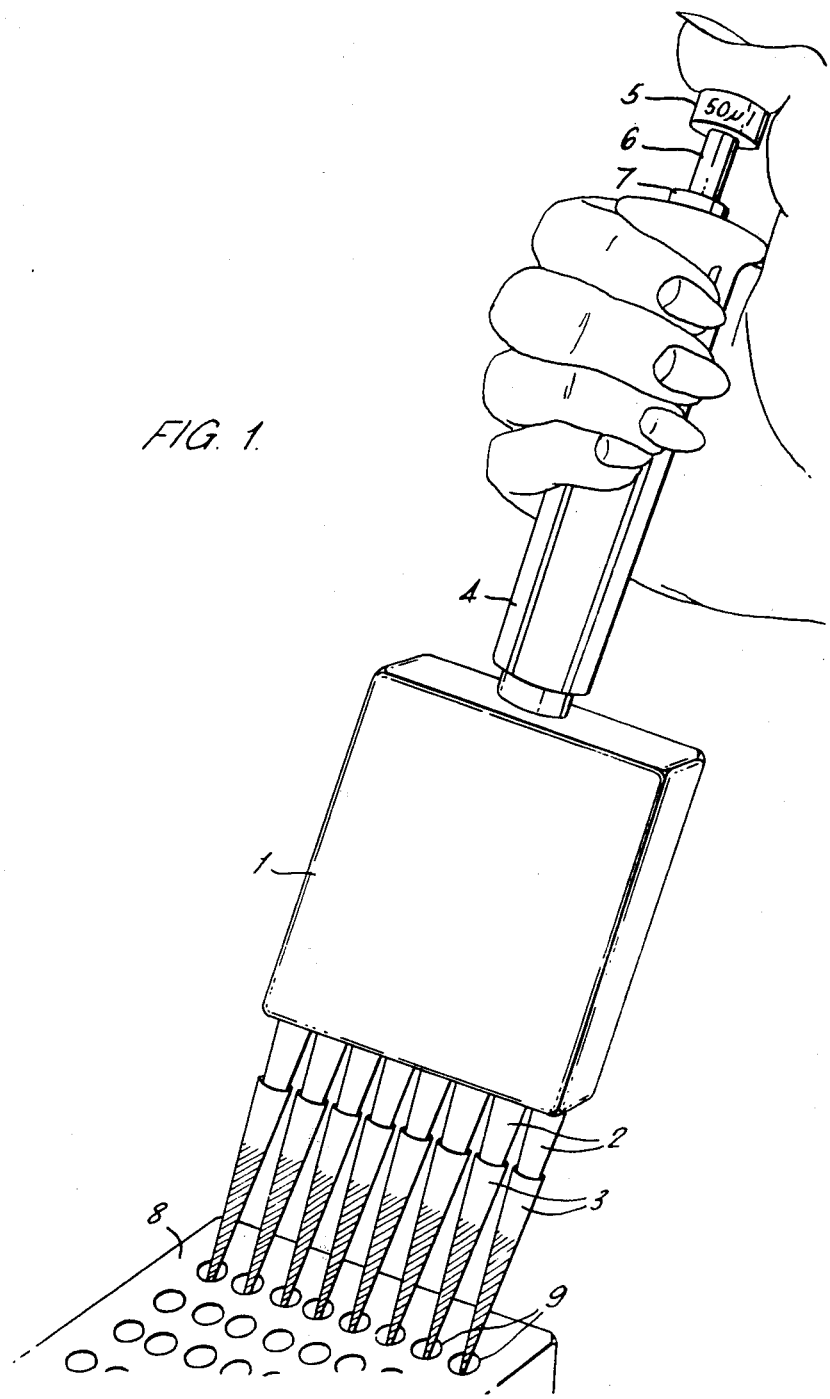
FIG. 1 is a perspective view of a multichannel pipette having the interchangeable handle of this invention.

FIG. 1 shows a multichannel pipette. The body portion 1 is provided with tip cone elements 2. Tip containers 3 are detachably connected to the tip cone elements. The handle part 4 includes, as visible in FIG. 1, a button 5, a button stem 6, and a secondary rest 7. The button 5 is pressed against the secondary rest 7, as the tip containers 3 of the multichannel pipette are submerged to the depth of about 0.5 to 1.0 cm in a liquid to be pipetted. Then, when the button 5 is allowed to rise to the upper position, due to the bias force of a first spring, the pistons suck a certain volume of the liquid from the pits 9 of the pit plate 8 into each tip container 3. The tip containers 3 are then emptied into the appropriate place, such as the next row of pits in the pit plate by pressing button 5 against the secondary rest 7 and continuing to press thereby depressing the button 5 some distance more against the secondary rest 7, which is biased upwardly by a second spring. After the tip containers have been emptied, the spring force restores the button 5 to its upper position.

Figure 2:
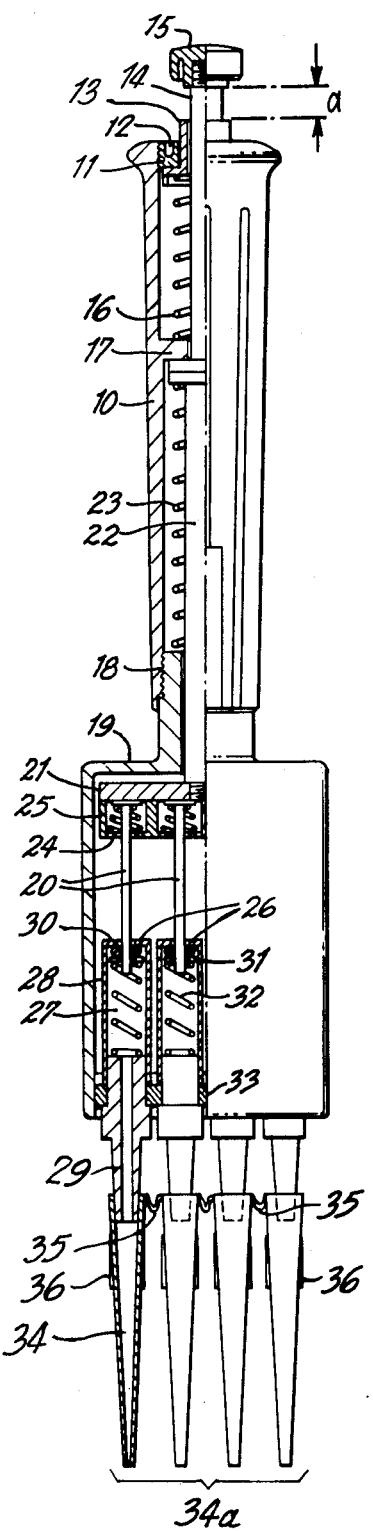
FIG. 2 is a partially cut away frontal view of the multichannel pipette, showing one embodiment of the tip container element of this invention.

FIG. 2 shows a 4-channel pipette. The handle part includes a housing 10, a calibration nut 11, with a space for a key 12 therein, a secondary rest 13, a button stem 14, a button 15, a secondary spring 16, which rests against a rest 17 for the secondary spring, placed in the housing 10. Secondary spring biases secondary rest 13 into its upper position to define stroke length "a." By turning the calibration nut 11 clockwise or anti-clockwise, it is possible to adjust the stroke length a of the button stem 14 so as to correspond a certain predetermined volume. The housing 10 of the handle part is by means of a thread fastened to the body portion 19. The body portion 19 includes a support disk 21 for the pistons 20, to which disk the activating rod 22 of the handle is fastened. The activating rod 22 is forced to the upper position by the bias force of a primary spring 23. The bottom plate 24 of the pistons 20 is fastened to the support disk 21. Support springs 25 force the pistons 20 against the support disk 21. The pistons 20 can move somewhat in the lateral direction. The force of the support springs 25 of the pistons 20 is dimensioned so that it is higher than the friction force created by the corresponding O ring 26 which surrounds each piston 20 and seals the piston in cylinder 28. The pistons 20 move in cylinder spaces 27 of their own. The cylinder space 27 is surrounded by a cylinder housing 28, which connects to and communicates with the tip cone 29. The O ring 26 is supported against the end 30 of the cylinder housing 28 by an O ring support 31 and is biased in place by a support spring 32. The force of the support spring 32 is higher than the frictional force caused by the O ring 26 of the piston 20. The cylinder housings 28 and the tip cones 29 constituting their extensions are fastened to a support disk 33, which is, on the other hand, fastened to the body portion 19.

The bases of the conical tip containers 34 are detachably connected over tip cone elements 29 to form an airtight seal with such elements. In accord with the present invention, the bases of the tip containers 34 are linked together in a linear configuration by small flexible connecting members or isthmuses 35 to form a tip container element 34(a). The connecting members are preferably longer than the distance between adjacent tip cone elements 29. This will cause the connecting members 35 to bow slightly as shown in FIG. 2 when the tip containers are connected to the tip cone elements 29.

When the individual tip containers 34 have their bases connected together by connecting member 35 they form elongated tip container elements 34(a) which nest inside of each other for easy packing and shipping. Projecting members 36 may be provided on the conical outer surface of each tip container. The presence of projecting members 36 prevents an excessively tight packing of the tip container elements within each other during shipping. Tip container elements such as those of FIG. 2, including connecting members 35 and projections 36 can be manufactured by injection molding from any flexible plastic material. Many such materials are known to those skilled in this art.

A user may cut or tear the tip container element 34(a) through one of the connecting members 35 at any desired point to detach any desired number of tip containers to fit a given configuration of tip cones on a multichannel pipette. Since the connecting members 35 are preferably made somewhat longer than necessary, a tip container element including a given number of tip containers can be used with pipettes having differing distances between their cone tips 29. Since the plastic material used for the tip container elements is flexible, the connecting element can be made to bow more or less depending on the distance between the tip cone elements.

A second more elaborate tip container element 13(a) is shown in FIG. 3. This element is configured to fit a multiple channel pipette having four tip cones. In this embodiment, two parallel flexible connecting members 15(a) are provided. A plurality of cross members 12(a) extend between the connecting members 15a. The individual tip containers 14(a) extend downwardly from the center of each cross member 12(a).

As in the embodiment of FIG. 2, the configuration shown in FIG. 3 may be made in any desired length by injection molding of a flexible plastic material. Again, the length of the connecting members 15(a) between the cross members 12(a) is made longer than necessary so that connecting members 15(a) bow out as much as necessary when attached to a configuration of tip cones.

The connecting members 15(a) can again be cut or torn to provide a tip container element of the desired length.

The portions of the cross members 12(a) which extend outwardly from the tip containers together with the connecting members 15(a) define handle extensions. These handle extensions permit the user of the pipette to mount and dismount the tip container element 13(a) without the need to touch any of the tip containers 14(a). This is advantageous both to prevent contamination of the liquid to be pipetted by contact with tip containers which have been touched or to prevent contamination of the user's hands by contact with potentially dangerous substances which have been pipetted.

A third embodiment of the tip container element of this invention is shown in FIG. 4. This embodiment 16(a) includes continuous parallel connecting members 19(a) which extend along the sides of the element and cross members 20(a) extending between the connecting members 19(a). The cross members 20(a) differ in configuration from those employed in the embodiment of FIG. 3. The connecting members 20(a) include two relatively narrow strips 22(a) at their points of connection with the parallel connecting members 19(a) and an enlarged central portion 24(a) disposed about the point of connection with each of the tip container elements 18(a). The central portion 24(a) is preferably a four sided planar surface such as a square or rectangle with the opening 21(a) to the tip container approximately at its center. As a result of the configuration of the cross members 20(a) apertures 26(a) in the approximate shape of the Roman numeral I are defined through the planar surface 17(a) of the tip container element 16(a) between each adjacent tip container element 18(a).

As in the prior embodiments, the device of FIG. 3 is preferably injection molded of a suitable flexible plastic material. Because of the apertures, 26(a), the connecting members 19(a) are again free to flex or bend when attached to an arrangement of tip cones. Although the element 16(a) is configured for four tip containers it is to be understood that this element can be made in any reasonable desired length and can be torn or cut through apertures 26(a) to obtain an element of the desired length.

The extending portions, such as connecting members 19(a) of the embodiment 16(a) of FIG. 4 form handle extensions by which the device can be mounted on or removed from a multichannel pipette. The advantages of this feature were discussed above with reference to the embodiment of FIG. 3.

As in the embodiment shown in FIG. 2, the tip container elements of FIG. 3 and FIG. 4 may be nested for economical shipping. If desired, projections such as 36 in FIG. 2 may be added to the sides of the individual tip container elements in these embodiments to prevent too tight a packing of these elements.

We claim:

1. A tip container element which is detachably connectable to the cone tips of a multichannel pipette, said element comprising a plurality of hollow truncated conical tip containers, which are linked together in a linear configuration, each of said tip containers having a base portion which is detachably connectable to one of the tip cones of said multichannel pipette; and connecting means linking said tip containers, said connecting means including two substantially parallel strip-like connecting members of a flexible material and a plurality of cross members extending between said connecting members, the bases of said tip containers being connected to and extending outwardly respectively from said cross members.

2. A tip container element as claimed in claim 1 in which each of said tip containers includes at least one projecting member connected to and extending outwardly from its outer longitudinal surface at a point adjacent to said base portion.

3. A tip container element as claimed in claim 1 in which the length of said connecting members between adjacent cross members is greater than the distance between adjacent cone tips of said multichannel pipette.

4. A tip container element as claimed in claim 1 in which each of said cross members includes a central portion having an aperture defining the input to the base of one of said tip containers.

5. A tip container element as claimed in claim 4 in which said portion of said cross member comprises a planar member.

* * * * *